United States Patent [19]

Ekholm

[11] 4,050,454

[45] Sept. 27, 1977

[54] CHIROPRACTIC TABLE

[75] Inventor: Carl Roger Ekholm, Elgin, Ill.

[73] Assignee: Williams Manufacturing Company, Elgin, Ill.

[21] Appl. No.: 698,963

[22] Filed: June 23, 1976

[51] Int. Cl.[2] .......... A61F 5/00
[52] U.S. Cl. .......... 128/70
[58] Field of Search .......... 128/68, 68.1, 70, 72-74

[56] References Cited

U.S. PATENT DOCUMENTS

| | | | |
|---|---|---|---|
| 2,150,519 | 3/1939 | Rogers et al. | 128/72 |
| 2,819,132 | 1/1958 | Rock | 128/70 |
| 3,092,102 | 6/1963 | Thompson | 128/70 |
| 3,993,051 | 11/1976 | Maruyama | 128/70 X |

*Primary Examiner*—Lawrence W. Trapp

*Attorney, Agent, or Firm*—Arnstein, Gluck, Weitzenfeld & Minow

[57] ABSTRACT

A table for use in administering chiropractic adjustments including at least one column mounting a body support and vertically movable relative to a base. Detent means bear against the column. A first air cylinder serves to elevate the column. A second air cylinder imposes a force against the detent means to provide a braking effect to hold the column at the upper limit of travel when the column is raised with a patient lying in part on the body support. When air pressure is shut off to both cylinders, the first cylinder retracts and air pressure is trapped in the second cylinder. The force imposed by the air pressure in the second cylinder to maintain the braking effect is substantially equal to the force required to lift the weight of the patient carried on the body support. The braking effect is overcome when a chiropractic thrust is applied to the body of a patient.

7 Claims, 5 Drawing Figures

FIG. 1
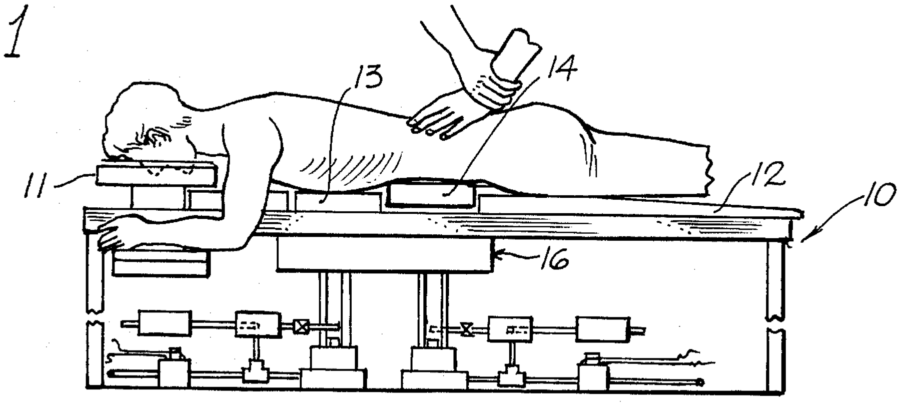
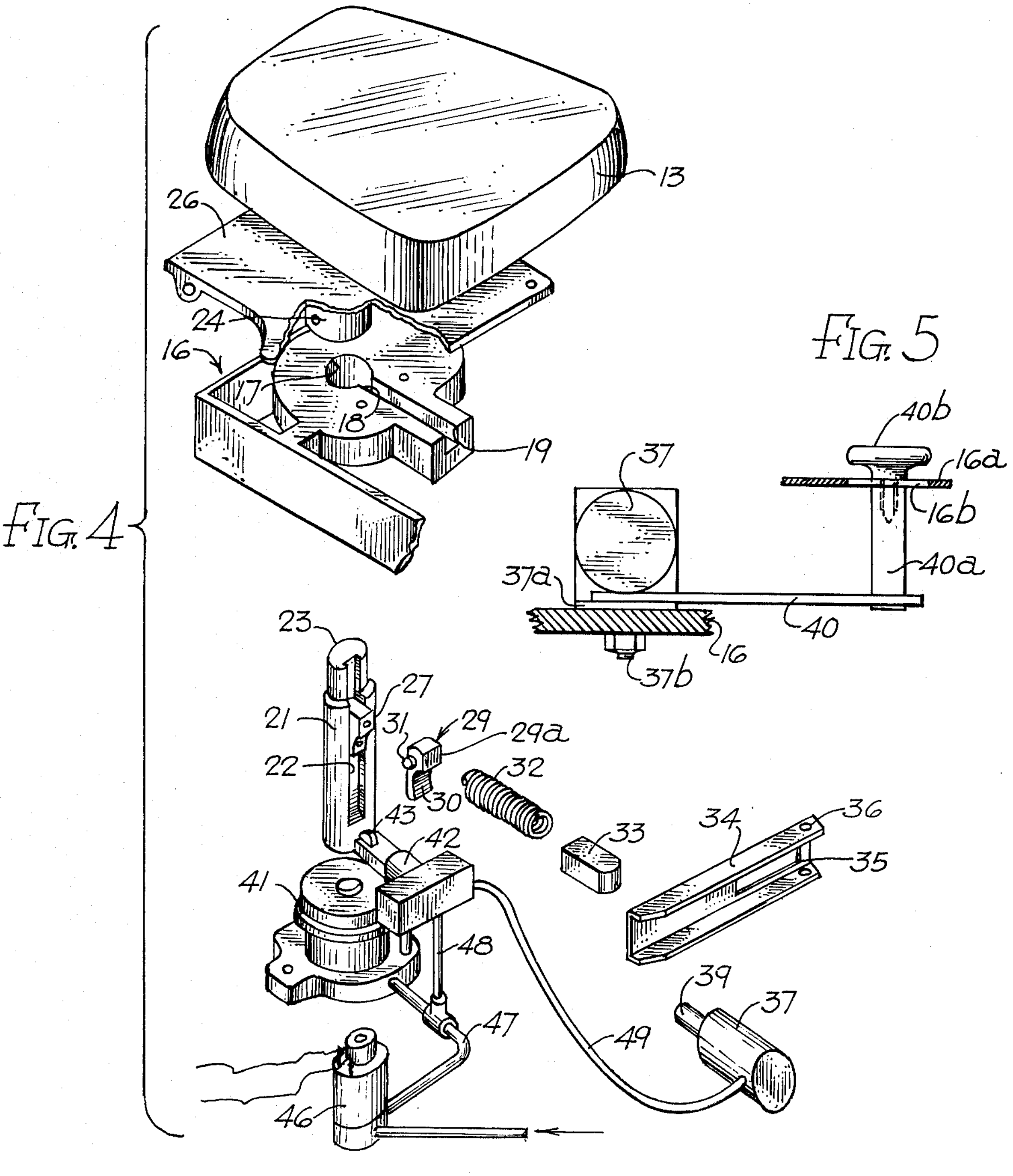
FIG. 4
FIG. 5

CHIROPRACTIC TABLE

BACKGROUND OF THE INVENTION

The present invention relates to tables for use by chiropractors in administering chiropractic adjustments of the human spine to correct subluxations of the vertebrae therein or other special ailments.

In the use of former chiropractic tables, as shown in U.S. Pat. No. 3,092,107, two separate cushion sections between the head and leg sections are mounted upon separate vertical columns or cushion supports with spring loaded detent latching elements bearing against the columns to hold them in raised positions. A manually operable cam is utilized to increase or decrease the pressure of the detents upon the columns. This pressure is adjusted to balance the weight of the different body areas of the subject being treated to hold such body areas in upraised position and in suspension until moved downwardly a limited distance by a force applied by the hands of the chiropractor to effect an adjustment or to correct subluxations of the vertebrae. The applied force overcomes the latching effect on a column permitting a cushion section to drop.

Adjustment of the pressure on the latching elements for patients of different weight conditions and anatomical structures involves an element of guess work on the part of the chiropractor to obtain the desired resistance to the reaction of his thrust so as to minimize discomfort to the patient and also to the chiropractor.

The prime object of the present invention is to eliminate the use of a manually controlled means, such as a cam, for adjusting the pressure on the latching element, and to utilize instead an auxiliary air cylinder deriving air pressure from the main air cylinder which is employed for elevating the vertical column. The air pressure entering the main air cylinder when the vertical column is being elevated is directly proportional to the weight of the patient. This same air pressure is bled into the auxiliary air cylinder and is utilized for imparting desired pressure on the latching element for controlling the resistance to movement of the vertical column, thereby automatically providing desired optimum conditions for administering chiropractic adjustments.

Additionally, means are provided for adjusting the pressure on the latching element to obtain a heavier or lighter release in response to the thrust applied by the chiropractor. It is known that the force of a thrust applied by a chiropractor will vary with different individuals. The purpose of such an adjustment is to coordinate or balance the release of the latching element with the force of the thrust so as to avoid injury to the patient.

BRIEF DESCRIPTION OF THE DRAWINGS

FIG. 1 is a side elevational view of a chiropractic table with a patient lying face down thereon and with one of the intermediate cushion sections in elevated position.

FIG. 4 is a fragmentary partially exploded diagrammatic view illustrating the components of my invention, and FIG. 5 is an end elevational view, partly in cross section of a detail.

BRIEF DESCRIPTION OF A PREFERRED EMBODIMENT

The chiropractic table 10 embodying my invention generally is similar to that shown in U.S. Pat. No. 3,092,102, and includes cushioned head and leg supporting sections 11 and 12 and two intermediate cushioned sections 13 and 14. My invention is specifically related to novel means for controlling the resistance to downward movement of the two intermediate cushioned sections 13 and 14. Since the means for operating each of the cushioned sections 13 and 14 are identical, only one of the means will be described and similar primed numerals will be used to identify corresponding parts of the other means.

Figure 2:
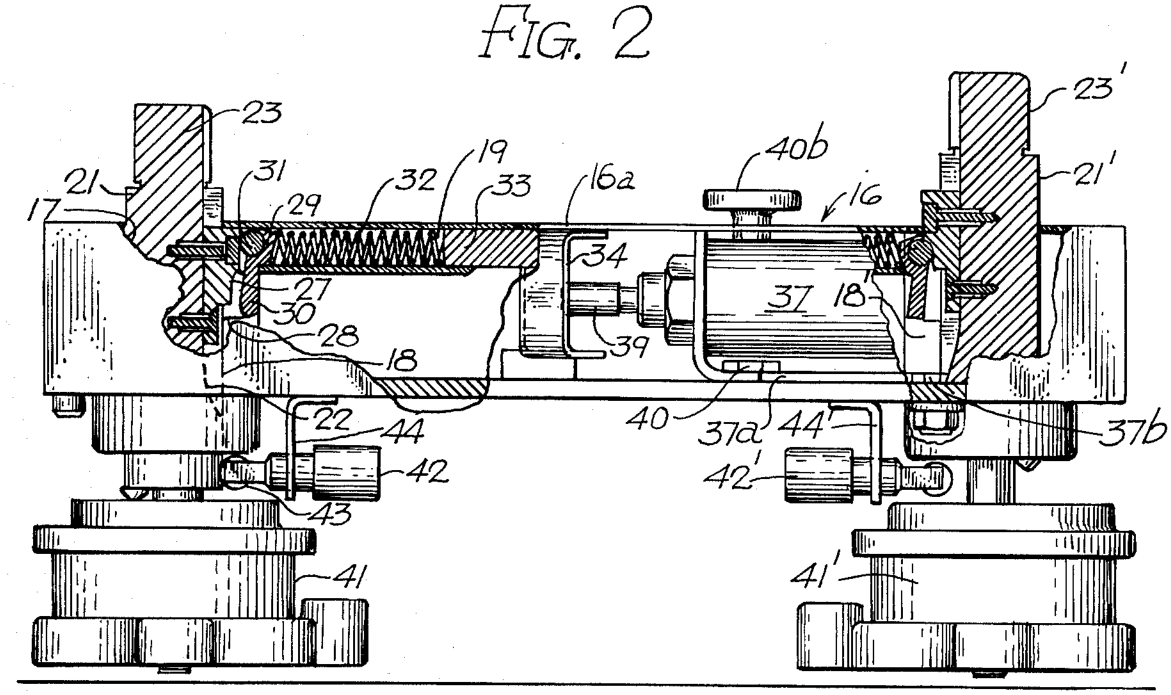
FIG. 2 is a fragmentary elevational view, partly in cross section, of a chiropractic table embodying my invention, with some of the parts eliminated for clarity of illustration.
Figure 3:
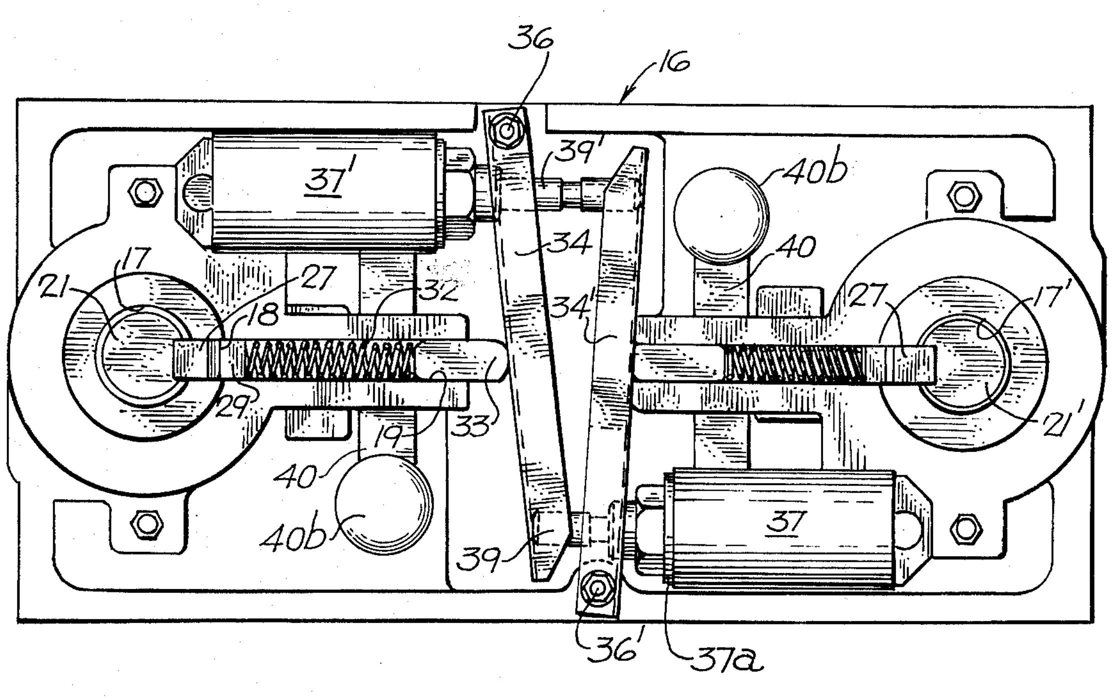
FIG. 3 is a top plan view of the structure illustrated in FIG. 2, with the cover panel removed.

The table 10 includes a generally rectangular intermediate base member 16 having a vertical bore 17 in each end portion. The bore 17 includes a vertical slot 18 which is in registration with a rectangular groove or channel 19 provided in the base member. A vertical column or cushion stem 21 is slidably mounted in the bore 17 and is provided with a longitudinally extending groove or channel 22 which is disposed in registration with the groove 19 in the base member 16. The upper end of column 21 has a reduced stepped portion 23 on which is supported a depending sleeve 24 of a cushion support 26 carrying the cushion 13. The channel 22 terminates short of the lower end of the column 21. A detent block 27, shaped substantially as shown, is rigidly secured in the channel 22 by a pair of bolts. As seen clearly in FIG. 2, the detent block 27 projects beyond the periphery of the column 21 and extends into the slot 18 of the bore. A brake bar or drop latch key 29 includes a head **29*a* provided with a transverse partially cylindrical passage providing a bearing for a roller 31 and also includes a depending leg 30. The leg 30 rests on an arcuate shoulder 28 constituting the bottom of slot 18. The head 29*a* is in registration with channel 19 and partially extends into the channel. The drop latch key 29 is tiltable about the axis of roller 31 within slot 18. A compression spring 32 contained within the channel 19 has one end in abutment with head 29*a* and urges roller 31 against detent block 27 to lock and retain the column 21, when raised in its highest position. The other end of spring 32 is engaged by a pusher block 33 which is slidable in channel 19 and which has a portion extending outwardly of the channel, as illustrated in FIG. 3**.

A channeled rocker are 34 is pivoted to the base member 16, as at 36, and extends transversely of the base member 16 so as to engage against the exposed end of the pusher block 33. A pneumatic latching cylinder 37 is mounted on a bracket **37*a* which is pivotally supported on the base member 16, as at 37*b*, with the piston rod 39 of cylinder 37 engaging the distal end of the rocker arm 34. As seen in FIG. 5, a link 40 is pivotally connected, at one end, to bracket 37*a*, the opposite end of the bracket carrying a spacer member 40*a* having internal threads. Said spacer member cooperates with a threaded stem fixed to an adjusting knob 40*b*. The threaded stem passes through an elongated slot 16*b* in the cover panel 16*a*. Bracket 37*a* may be rocked about axis 37*b* and locked in a position of adjustment by tightening knob 40*b***.

A pneumatic cocking cylinder 41 is suitably mounted below and in vertical registration with the cushion stem 21. The function of the cocking cylinder is to elevate the cushion stem 21 and with it the cushion 13, as will be hereinafter explained. A two-way valve 42 having an actuating stem provided with a roller 43 at its end is supported on a bracket 44 depending from the base member 16 and is adapted to engage and to be actuated by the movement of the cushion stem 21.

The cocking cylinder 41 is connected to a conventional pressurized air supply through a three-way solenoid operated valve 46. The two-way valve 42 is connected into the line 47 leading from the solenoid valve 46 to the cocking cylinder 41 by a conduit 48 and also is connected to the latching cylinder 37 by a conduit 49.

As illustrated in FIGS. 3 and 4, two identical sets of operative components are associated with the intermediate base member 16 of table 10. As seen in FIG. 3, the rocker arms 34 and 34' are rockably supported at opposite sides of the base member 16 and are disposed substantially in the same horizontal plane. The web portion of the rocker arm 34 is slotted for a portion of its length, as at 35, to accommodate the piston rod 39' of the opposite apparatus. In each case, the end portion of each piston rod 39, 39' projects through a slot 35, 35' in order to engage its associated rocker arm 34, 34'. As previously noted, each of the latching cylinders 37, 37' is pivotally supported on the base member 16 to rock about a vertical axis so as to vary the point of application of pressure along the rocker arm 34, 34 thereby to vary the moment of force about the pivotal axis of the rocker arm. This adjustment is made by the chiropractor to balance the release of the latch key 29 with the force of the thrust applied by the chiropractor so as to avoid injury to the patient. Generally this should be a one time adjustment and should be changed only as the force of the applied thrust changes.

In the operation of my invention, with a patient lying in prone position on the table 10, one or both of the cushion sections 13, 14 is raised to its uppermost position. In FIG. 2, the cushion stem 21 on the left hand side of the intermediate table section is shown in lowered or retracted position while the cushion stem 21' on the right hand side is shown in its uppermost or elevated condition. The cushion stem 21 is caused to be elevated by operating the solenoid valve 46 to admit pressurized air (60–80 p.s.i. line pressure) into the cocking cylinder 41, the piston rod of which engages the lower end of the cushion stem 21. The weight of the patient is balanced by the air pressure in the cocking cylinder 41, since the pressure in said cylinder during the upward movement of the cushion stem 21 is directly proportional to the weight of the patient. Concurrently, as the cushion stem 21 travels upwardly, the roller 43 is engaged with the cushion stem 21 and the two-way valve 42 is conditioned to admit pressurized air into the latching cylinder 37. Just short of the limit of the upward travel of the cushion stem 21, the roller 43 becomes disengaged from the cushion stem 21, as shown in FIG. 2, thus, causing valve 42 to cut off the admission of pressurized air into the latching cylinder 37 but trapping pressurized air therein. When the cushion stem 21 reaches its uppermost position, cylinder 41 which is provided with an internal return spring, retracts the piston rod of cocking cylinder 41 leaving the cushion stem 21 retained in its uppermost position by the drop latch key 29 which is caused to bear against the detent block 27 by the spring 32. The trapped pressurized air in the latching cylinder 37 through the piston rod 39, rocker arm 34, pusher block 33 and spring 32, maintains pressure on the drop latch key 29 creating a braking effect to hold the cushion stem 21 upwardly. The amount of pressure on the spring 32 and drop latch key 29 is directly proportional to the trapped pressure in the latching cylinder 37. The pressure of the trapped air in the latching cylinder 37 is less than the incoming line pressure. After the admission of pressurized air in cylinder 37 is cut off, a balanced condition is achieved corresponding to the pressure required for lifting the weight of the patient and such condition is maintained regardless of the pressure condition in cylinder 41. It will be understood that there is a particular relationship between the effective areas of pistons in cylinders 41 and 37 and that the angular adjustment of cylinder 37 in relation to lever 34 will afford a degree of flexibility permitting variation of this relationship.

As the chiropractor exerts pressure on the patient, the latching or braking effect is overcome and the cushion 13 and cushion stem 21 now may drop a distance of approximately ½ inch. As the cushion stem 21 begins to move downwardly upon the application of a thrust on the patient by the chiropractor, the valve 42 is caused to be actuated by engagement of the roller 43 with the cushion stem 21 to open the discharge port of valve 42 permitting the trapped air in the latching cylinder 37 to be exhausted. Lateral pressure on the cushion stem 21 now is relieved so that the cushion stem 21 and cushion 13 may drop freely. When the cushion stem bottoms the chiropractic adjustment is completed. It is noted that spring 32 which is interposed between head **29*a* and a pusher block 33 is compressible. Thus, the drop latch key 29 is immediately responsive to afford clearance for the release of the cushion stem 21, even before there is any retractive movement of the piston rod 39**, which is slower acting and which ultimately will fully retract within the cylinder.

Various changes coming within the spirit of my invention may suggest themselves to those skilled in the art; hence, I do not wish to be limited to the specific embodiments shown and described or uses mentioned, but intend the same to be merely exemplary, the scope of my invention being limited only by the appended claims.

I claim:

1. In a table for use in administering chiropractic adjustments, a base member having a bore, a vertical column slidably mounted in said bore, a body support mounted on said column, detent means bearing against said vertical column, a first air cylinder for elevating said vertical column, a second air cylinder bearing against said detent means to provide a braking effect to hold said column at the upper limit of travel when raised with a patient lying in part on said body support, conduit means connecting said first and second cylinders to a source of air pressure, means for retracting said first cylinder when said column has reached its upper limit of travel, means for cutting off the supply of air pressure to said second cylinder and for trapping air pressure in said second cylinder substantially proximate the upper limit of travel of said column, the trapped air pressure in said second cylinder being substantially equal to the air pressure in said first cylinder required for lifting the weight of the patient carried on said body support.

2. The invention as defined in claim 1 in which the cut-off means includes valve means connected upstream of said second cylinder and responsive to the movement of said vertical column for controlling the flow of pressurized air into said second cylinder.

3. The invention as defined in claim 2 in which the valve means is operable to cut off the admission of pressurized air during the elevation of said column and to trap pressurized air in said second cylinder just before the column reaches the upward limit of its movement.

4. In a table for use in administering chiropractic adjustments, a base member having a bore, a vertical column slidably mounted in said bore, a body support mounted on said column, detent means bearing against the vertical column, first pneumatically operated means for elevating said column, second pneumatically operated means bearing against said detent means to provide a braking effect to hold said column at the upper limit of travel when raised with a patient lying in part on said body support, conduit means connecting said first and second pneumatically operated means to a source of air pressure, the air pressure in said second pneumatically operated means being substantially equal to the column elevating pressure in said first pneumatically operated means, means for trapping the air pressure in said second pneumatically operated means to maintain the braking effect after the source of air pressure has been cut off, said braking effect being overcome when a chiropractic thrust is applied to the body of the patient.

5. In a table for use in administering chiropractic adjustments, a base member having a bore having a vertical slot, a vertical column having a longitudinally extending channel and slidably mounted in said bore, said base member having a channel communicating with said slot and in registration with the column channel, a body support mounted on said column, a detent block secured in said column channel, a drop latch key having a head and a depending foot and tiltably mounted in said slot with the head being in registration with said base channel and with the foot resting on the bottom of said slot, said head carrying a bearing roller bearing against said detent block, spring means mounted in the base channel and bearing against said head to hold the column at the upper limit of movement, the improvement which comprises a first air cylinder for elevating said vertical column, a second air cylinder bearing against said spring means for controlling the compression of the spring means and its force as applied to the detent to control the braking effect on said column, first conduit means connecting said first air cylinder to a supply of pressurized air, second conduit means connecting said second air cylinder to said first conduit means, means for retracting said first cylinder when said column has reached its upward limit of travel, means for cutting off the supply of air pressure to said second cylinder and for trapping pressure in said second cylinder substantially proximate the upper limit of travel of said column, the trapped air pressure in said second cylinder being substantially equal to the air pressure in said first cylinder required for lifting the weight of the patient carried on said body support, said braking effect being overcome when a chiropractic thrust is applied to the body of a patient.

6. The invention as defined in claim 1 including a pivoted lever operatively engaged with said detent means and means for pivotally supporting said second cylinder for angular movement relative to said lever whereby to vary the movement of force applied to said detent means.

7. In a table for use in administering chiropractic adjustments, a base, a pair of columns vertically slidable relative to said base member, a body support mounted on each of said columns, detent means bearing against each of said columns, a first pair of air cylinders each for elevating a column, a second pair of air cylinders each bearing against a respective detent means to provide a braking effect to hold a column at the upper limit of travel when raised with a patient lying in part on said body supports, conduit means connecting respective first and second cylinders to a source of air pressure, means for retracting each of said first cylinders when a respective column has reached its upper limit of travel, means for cutting off the supply of air pressure to each of said second cylinders and for trapping air pressure in a second cylinder substantially proximate to the upper limit of travel of a respective column, the trapped air pressure in a second cylinder being substantially equal to the air pressure in a respective first cylinder required for lifting the weight of the patient carried on a respective body support, the braking effect being overcome when a chiropractic thrust is applied to the body of a patient.

* * * * *